United States Patent [19]
Blank et al.

[11] Patent Number: 4,716,042
[45] Date of Patent: Dec. 29, 1987

[54] STABILIZED COATED ASPIRIN TABLETS

[75] Inventors: Robert G. Blank, Vineland, N.J.; Ronald W. Miller, Huntingdon Valley, Pa.

[73] Assignee: American Home Products Corporation, New York, N.Y.

[21] Appl. No.: 874,956

[22] Filed: Jun. 16, 1986

[51] Int. Cl.$^4$ .............................................. A61K 9/28
[52] U.S. Cl. .................................... 424/474; 514/165
[58] Field of Search ................... 424/35, 474; 514/165

[56] References Cited

U.S. PATENT DOCUMENTS

| | | | |
|---|---|---|---|
| 2,101,867 | 12/1937 | Miller et al. | 514/165 |
| 2,801,951 | 8/1957 | Cooper | 514/165 |
| 3,256,111 | 6/1966 | Singiser | 424/35 |
| 3,981,984 | 9/1976 | Signorino | 424/35 |
| 4,001,390 | 1/1977 | Ohno et al. | 424/35 |
| 4,017,647 | 4/1977 | Ohno et al. | 424/35 |
| 4,167,558 | 9/1979 | Sheth et al. | 424/35 |
| 4,302,440 | 11/1981 | John et al. | 424/35 |
| 4,414,198 | 11/1983 | Michaelson | 424/35 |
| 4,555,399 | 11/1985 | Hsiao | 424/35 |

OTHER PUBLICATIONS

Stozek, Thomasz, "Decomposition of Acetylsalicylic Acid and the Possibilities of its Stabilization in Solid Forms of the Drug", Farmacja Polska, No. 8, pp. 771–775, (1972).

Nazareth, M. R. et al, "Stability of Aspirin in Aspirin, Phenacetin, and Caffeine Tablets", J. of Pharm. Sci., vol. 50, No. 7, Jul. 1961.

Delonca, H. et al, "Influence of Excipients and Storage Conditions on Conservation of Drugs; I. Case of Acetylsalicylic Acid Based Tablets", Journal de Pharmacie de Belgique, vol. 24, pp. 243–252, (1969).

Delonca, H. et al, "Influence of Excipients and Storage Conditions on Conservation of Drugs; II. Case of Acetylsalicylic Acid Based Capsules", Journal de Pharmace de Belgique, No. 24, pp. 317–331, (1969).

Guttman, D. E., "Heterogeneous Catalysis of Aspirin Degradation in Chloroformic Solution and its Relationship to the Determination of Salicylic acid in Buffered Aspirin Products", J. of Pharmaceutical Sciences, vol. 57, No. 10, pp. 1685–1689, Oct. 1968.

Zoglio, M. A. et al, "Pharmaceutical Heterogeneous Systems III", Journal of Pharmaceutical Sciences, vol. 57, No. 11, pp. 1877–1880, (1968).

Blank, R. G. Affidavit.

Primary Examiner—Shep K. Rose
Attorney, Agent, or Firm—John W. Routh

[57] ABSTRACT

Coated aspirin tablets/caplets are provided wherein acetylsalicylic acid decomposition is inhibited by incorporation therein prior to coating of citric, alginic or glutamic acids of mixtures thereof.

4 Claims, No Drawings

STABILIZED COATED ASPIRIN TABLETS

BACKGROUND OF THE INVENTION (a) Field of the Invention

This invention relates to coated aspirin tablets or caplets stabilized against degradation of acetylsalicylic acid. More particularly, this invention relates to coated aspirin tablets or caplets wherein decomposition into acetic acid and salicylic acid is inhibited by incorporation therein prior to coating of a small amount of citric acid, alginic acid, glutamic acid or admixtures of any two or three thereof.

(b) Prior Art

Alginic acid is disclosed in admixture with aspirin, phenacetin, caffeine starch and talc and further with these ingredients and polyvinylpyrollidone in an article by M.R. Nazareth et al entitled "Stability of Aspirin in Aspirin, Phenacetin, and Caffeine Tablets" in Journal of Pharmaceutical Sciences, Vol. 50, No. 7, July 1961. The article concludes with the statement: "Taking appearance, disintegration time, and stability of aspirin into consideration, formula B [without alginic acid] emerges as the best of the four formulations studies and can easily be used in preparation of tablets of aspirin, phenacetin, and caffein."

The "United States Pharmacopeia" 21st rev. Mack Publishing Company, Easton Pa. 1985 at page 79 specifies that aspirin tablets contain not less than 95.0% and not more than 105.0% of the labelled amount of acetylsalicylic acid ($C_9H_8O_4$). Aspirin tablets are known to decompose slowly into acetic acid and salicylic acid. The assay at the said USP page 79 for Free Salicyclic Acid indicates that for tablets not more than 0.3% is found and for coated tablets not more than 3.0% is found. The rate of decomposition is slow but in order for the tablets to meet their labelled shelf-life according to USP standards, the shelf life is sometimes shortened to be within safe limited. Recently it has been found that with the advent in the market place of film coated tablets, such as those described in U.S. Pat. No. 4,302,440, the decomposition of such tablets appears to be accelerated by the coating in that the acetic acid formed by the decomposition is trapped within the tablet and causes further decomposition. Also, the acetic acid seems to impart a vinegar taste to the coated tablets after standing. There is therefore a need in the art for an inhibitor of acetylsalicylic acid decomposition in order to extend the shelf life of aspirin tablets and caplets, either film coated or enteric coated, the latter as described in U.S. Pat. No. 4,017,647.

SUMMARY OF THE INVENTION

According to this invention coated aspirin tablets or caplets have been provided which are inhibited against decomposition of acetylsalicylic acid by having incorporated into the aspirin formulation prior to coating of a small amount of citric acid, alginic acid, glutamic acid or mixtures of any two or three thereof, i.e. about 0.5% to 3% by weight based upon the weight of aspirin in the coated tablet or caplet.

DETAILS OF THE INVENTION

Typical coated tablet or caplet formulations having improved stability against degradation of acetylsalicylic acid according to this invention are described in the following examples.

EXAMPLE 1

The formulation of this example contains the materials shown below in milligrams per caplet.

| Ingredients | Mg/Caplet |
| --- | --- |
| Aspirin 20/40 mesh USP | 400.0 |
| Caffeine, Anhydrous NF | 32.0 |
| Microcrystalline Cellulose, NF | 72.1 |
| Starch, NF | 15.6 |
| Sodium Lauryl Sulfate, NF | 0.3 |
| Alginic Acid (Kelacid) NF | 12.0 |
| Citric Acid (powdered) USP | 12.0 |
| | 544.0 |

The above ingredients as part of a larger 13.5 kilogram batch were admixed to form a compression mix in a Marion Mixer for 5 minutes and then compressed on a Stokes Rotary Press using caplet shaped tooling 0.290 inch by 0.625 inch by 0.035 inch with 2.6 to 2.7 tonnage at a speed of 3000 caplets per minutes.

The compression range characteristics of these caplet cores were as follows:

| | |
| --- | --- |
| Target weight = | 544.0 mg/caplet |
| Thickness range = | 0.188–0.193 inch |
| Hardness range = | 6 to 9 SCU |
| Disintegration = | 6 to 40 seconds |
| Friability = | 0% in 4 minutes / 2.20% in 15 minutes |

The caplet cores as prepared above were then subjected to a double coating operation involving a first coat of the Klucel EF brand of hydroxypropyl cellulose marketed by Hercules, Inc. of Wilmington, Delaware and a second coat of Methocel brand of hydroxypropyl-methyl- cellulose, a mixture of the Methocel E-5 and Methocel E-15 grades, marketed by Dow Chemical Company Midland, Michigan.

The coating procedure was as follows:

Hydroxypropyl Cellulose Phase

The core caplets were microcoated in a 24 inch pan Hi-Coater brand of tablet coating machine. The coating material was comprised of 0.5% hydroxypropyl cellulose by weight in a 12% solids dispersion in water, mixed and allowed to hydrate. Sufficient microcrystalline cellulose was added to prevent sticking of the caplets to the pan and to each other. The coater operating conditions were as follows:

| | |
| --- | --- |
| Nozzle opening | 1.5 mm |
| Atomization | 110 |
| Pattern | 50 |
| Spray rate | 40 ml./min. |
| RPM | 4.5 to 5.5 |
| Air Inlet | 72–78° C. |
| Air Outlet | 40–47° C. |
| Inlet and Exhaust Dampers - Open | |

Each caplet was coated on the average with 2.720 mg of hydroxypropyl cellulose and 0.680 mg of microcrystalline cellulose.

Hydroxypropyl Methylcellulose Phase

The core caplets previously coated with hydroxypropyl cellulose were then subjected to a second coating with hydroxypropyl methylcellulose using the same 24 inch pan and the same coating machine as were used for the first coat. The coating material was comprised of 0.5% hydroxypropyl methylcellulose by weight in a 12% solution in water, mixed and allowed to hydrate. The coater operating conditions were as follows:

| Nozzle opening | 1.5 mm |
| --- | --- |
| Atomization | 110 |
| Pattern | 50 |
| Spray rate | 45 ml./min. |
| RPM | 6 |
| Air Inlet | 76–78° C. |
| Air Outlet | 46–47° C. |
| Inlet and Exhaust Dampers - Open | |

The coating material also contained other ingredients such that each caplet was coated on the average with the following in milligrams per caplet;

| Hydroxypropyl methylcellulose (Methocel E-5) | 1.813 |
| --- | --- |
| Hydroxypropyl methylcellulose (Methocel E-15) | .907 |
| Triacetin (Food grade) | .544 |
| Sodium Lauryl Sulfate (Empicol 303) NF | .023 |
| and the theoretical total caplet weight was | 550.687 |

The USP average caplet weight was 545 mg, the thickness was 0.187 inch to 0.193 inch, the disintegration time was 6 to 40 seconds with plugs, the hardness was 9 to 13 SCU and the friability was 0% at 4 minutes.

EXAMPLE 2

The formulation of this example contains the materials shown below in milligrams per caplet. The formulation differs from that in Example 1 in that the alginic acid and citric acid amounts have been lowered from 12 milligrams each to 6 milligrams each.

| Ingredients | Mg/Caplet |
| --- | --- |
| Aspirin 20/40 mesh USP | 400.0 |
| Caffeine, Anhydrous NF | 32.0 |
| Microcrystalline Cellulose, NF | 72.1 |
| Starch, NF | 15.6 |
| Sodium Lauryl Sulfate, NF | 0.3 |
| Alginic Acid (Kelacid) NF | 6 |
| Citric Acid (powdered) USP | 6 |
| | 532.0 |

The above ingredients as part of a larger 13.5 kilogram batch were admixed to form a compression mix in a Marion Mixer for 5 minutes and then compressed on a Stokes Rotary Press using caplet shaped tooling 0.290 inch by 0.625 inch by 0.035 inch with 2.6 to 2.7 tonnage at a speed of 3000 caplets per minute.

The compression range characteristics of these caplet cores were as follows:

| Target weight = | 532.0 mg/caplet |
| --- | --- |
| Thickness range = | 0.182–0.187 inch |
| Hardness range = | 7 to 9.5 SCU |
| Disintegration = | 30 seconds |
| Friability = | 1.25% in 4 minutes |
| | 1.75% in 15 minutes |

The caplet cores as prepared above were then subjected to a double coating operation involving a first coat of the Klucel EF brand of hydroxypropyl cellulose marketed by Hercules, Inc. of Wilmington, De. and a second coat of Methocel brand of hydroxypropylmethyl- cellulose, a mixture of the Methocel E-5 and Methocel E-15 grades, marketed by Dow Chemical Company Midland, Mich.

The coating procedure was as follows:

Hydroxypropyl Cellulose Phase

The core caplets were microcoated in a 24 inch pan Hi-Coater brand of tablet coating machine. The coating material was comprised of 0.5% hydroxypropyl cellulose by weight in a 12% solids dispersion in water, mixed and allowed to hydrate. Sufficient microcrystalline cellulose was added to prevent sticking of the caplets to the pan and to each other. The coater operating conditions were as follows:

| Nozzle opening | 1.5 mm |
| --- | --- |
| Atomization | 110 |
| Pattern | 50 |
| Spray rate | 40 ml./min. |
| RPM | 4.5 to 5.5 |
| Air Inlet | 76–78° C. |
| Air Outlet | 40–46° C. |
| Inlet and Exhaust Dampers - Open | |

Each caplet was coated on the average with 2.720 mg of hydroxypropyl cellulose and 0.680 mg of microcrystalline cellulose.

Hydroxypropyl Methylcellulose Phase

The core caplets previously coated with hydroxypropyl cellulose were then subjected to a second coating with hydroxypropyl methylcellulose using the same 24 inch pan and the same coating machine as were used for the first coat. The coating material was comprised of 0.5% hydroxypropyl methylcellulose by weight in a 12% solution in water, mixed and allowed to hydrate. The coater operating conditions were as follows:

| Nozzle opening | 1.5 mm |
| --- | --- |
| Atomization | 110 |
| Pattern | 50 |
| Spray rate | 45 ml./min. |
| RPM | 6 |
| Air Inlet | 77–79° C. |
| Air Outlet | 46–47° C. |
| Inlet and Exhaust Dampers - Open | |

The coating material also contained other ingredients such that each caplet was coated on the average with the following in milligrams per caplet;

| Hydroxypropyl methylcellulose (Methocel E-5) | 1.773 |
| --- | --- |
| Hydroxypropyl methylcellulose (Methocel E-15) | .887 |
| Triacetin (Food grade) | .532 |
| Sodium Lauryl Sulfate (Empicol 303) NF | .023 |
| and the theoretical total caplet weight was | 538.540 |

The formulations of Examples 1 and 2 were then subjected to room temperature accelerated stability testing by standard techniques, i.e. by enclosing appropriate packaged samples in chambers maintained at room temperature and at 37° C. and 75% relative humidity for three months and then opening the package and assaying for free salicylic acid levels in accordance with the test described in the United States Pharmacopeia, 21st rev. pages 78 and 79.

Samples of the caplets of Example 1 were placed in each of 23 cc and 85 cc white, high density polyethylene bottles equipped with a polypropylene safety snap cap and a 75M brand foil liner covering the bottle opening. Samples of caplets of Example 2 were placed in identically equipped 23 cc and 85 cc bottles and all samples were placed in the test chambers.

As a control, aspirin tablets were employed which were made similarly as the caplets of Example 1 containing 400 mg aspirin per tablet and with the same relative proportions of ingredients but without alginic acid or citric acid. The Stokes Rotary Press used a tablet shaped tooling 0.410 inch in diameter by 0.200 inch thick with 3.8 to 4.0 tonnage at a speed of about 3000 tablets per minutes. The tablet cores were then subjected to a single coating operation similarly as the second coating operation in Example 1. As in Examples 1 and 2, the hydroxypropyl methylcellulose coating material also contained other ingredients such that each tablet was coated on the average with the following in milligrams per tablet;

| | |
|---|---|
| Hydroxypropyl methylcellulose (Methocel E-5) | 3.47 |
| Hydroxypropyl methylcellulose (Methocel E-15) | 1.73 |
| Triacetin (Food grade) | 1.04 |
| and the theoretical total tablet weight was | 526.24 mg. |

The tablets were tested in three different types of packaging, a commercial 12 tablet tin, an Ivers Lee two tablet strip pack in 133 paper lined with polyethylene, and in an 87 cc white, polystyrene bottle equipped with a low density polyethylene snap cap and an HS035 liner covering the bottle opening.

The stability test results are shown in Table I below:

TABLE I

| | Free Salicylic Acid/Milligrams | |
|---|---|---|
| | 23 c.c. Bottle | 85 c.c. Bottle |
| Caplets of Example 1 | | |
| Room Temperature | 0.152 mg | 0.088 mg. |
| 37° C./75% R.H. | 0.626 mg. | 0.472 mg. |
| Caplets of Example 2 | | |
| Room Temperature | 0.196 mg. | 0.301 mg. |
| 37° C./75% R.H. | 0.640 mg. | 0.678 mg. |
| Tablets | Tin | Strip | Bottle |
| Room Temperature | 0.667 mg. | 0.798 mg. | 0.554 mg. |
| 37° C./75% R.H. | 2.12 mg. | 3.05 mg. | 2.72 mg. |

The results indicate that the combination of alginic acid and citric acid in the aspirin formulation inhibits the decomposition of acetylsalicylic acid in coated caplets.

EXAMPLE 3

The formulation of this example contains the materials shown below in milligrams per tablet. The formulation differs from that in Example 1 in that alginic acid alone was used in the amount of 12 milligrams per tablet.

| Ingredients | Mg/Tablet |
|---|---|
| Aspirin 20/40 mesh USP | 400.0 |
| Caffeine, Anhydrous NF | 32.0 |
| Microcrystalline Cellulose, NF | 72.1 |
| Starch, NF | 15.6 |
| Sodium Lauryl Sulfate, NF | 0.3 |
| Alginic Acid (Kelacid) NF | 12.0 |

The above ingredients as part of a 13.5 kilogram batch were processed similarly as in Example 1 and the theoretical tablet weight was 532.0 milligrams. The tablets were subjected to a single coating operation similarly as the second coating operation in Example 1 and the theoretical tablet weight after coating was 538.38 milligrams.

EXAMPLE 4

The formulation of this example contains the materials shown below in milligrams per tablet. The formulation differs from that in Example 1 in that citric acid alone was used in the amount of 12 milligrams per tablet.

| Ingredients | Mg/Tablet |
|---|---|
| Aspirin 20/40 mesh USP | 400.0 |
| Caffeine, Anhydrous NF | 32.0 |
| Microcrystalline Cellulose, NF | 72.1 |
| Starch, NF | 15.6 |
| Sodium Lauryl Sulfate, NF | 0.3 |
| Citric Acid (powdered) USP | 12.0 |

The above ingredients as part of a 13.5 kilogram batch were processed similarly as in Example 1 and the theoretical tablet weight was 532.0 milligrams. The tablets were subjected to a single coating operation similarly as the second coating operation in Example 1 and the theoretical tablet weight after coating was 538.38.

EXAMPLE 5

The formulation of this example contains the materials shown below in milligrams per tablet. The formulation differs from that in Example 1 in that glutamic acid alone was used in the amount of 12 milligrams per tablet.

| Ingredients | Mg/Tablet |
|---|---|
| Aspirin 20/40 mesh USP | 400.0 |
| Caffeine Anhydrous NF | 32.0 |
| Microcrystalline Cellulose, NF | 72.1 |
| Starch, NF | 15.6 |
| Sodium Lauryl Sulfate, NF | 0.3 |
| Glutamic Acid, NF | 12.0 |

The above ingredients as part of a 13.5 kilogram batch were processed similarly as in Example 1 and the theoretical tablet weight was 532.0 milligrams. The tablets were subjected to a single coating operation similarly as the second coating operation in Example 1 and the theoretical tablet weight after coating was 538.38.

The tablets of Examples 3,4 and 5 are also inhibited from decomposition with respect to acetylsalicylic acid by incorporation of 3% by weight of each of alginic, citric and glutamic acids.

We claim:

1. A film coated aspirin tablet/caplet containing as the active ingredient a material selected from the group consisting of aspirin and aspirin with caffeine wherein acetylsalicylic acid decomposition is inhibited by incorporation therein prior to coating of a small decomposition inhibiting amount of an acid selected from the group consisting of citric acid, alginic acid, glutamic acid and admixtures thereof, the coated tablet/caplet having been film or enteric coated from an aqueous solution of a film or enteric coating material.

2. The coated aspirin tablet of claim 1 wherein the decomposition inhibiting amount of the acid is 0.5% to 3% by weight based upon the weight of aspirin.

3. A coated tablet/caplet consisting essentially of aspirin as the active ingredient wherein acetylsalicylic acid decomposition is inhibited by incorporation therein prior to coating of a small decomposition inhibiting amount of an acid selected from the group consisting of citric acid, alginic acid, glutamic acid and admixtures thereof.

4. The coated aspirin tablet of claim 3 wherein the decomposition inhibiting amount of the acid is 0.5% to 3% by weight based upon the weight of aspirin.

* * * * *